United States Patent
Horwitz et al.

(10) Patent No.: US 9,234,899 B2
(45) Date of Patent: Jan. 12, 2016

(54) HUMAN βV-TUBULIN ANTIBODY AND METHODS OF USE

(71) Applicant: Albert Einstein College of Medicine of Yeshiva University, Bronx, NY (US)

(72) Inventors: Susan Horwitz, Larchmont, NY (US); Suzan Chao, Bronx, NY (US); Yihong Wang, Wayland, MA (US); Pascal Verdier-Pinard, Marseilles (FR); Hayley Maria McDaid, Riverdale, NY (US)

(73) Assignee: Albert Einstein College of Medicine, Inc., Bronx, NY (US)

( * ) Notice: Subject to any disclaimer, the term of this patent is extended or adjusted under 35 U.S.C. 154(b) by 80 days.

(21) Appl. No.: 13/912,266

(22) Filed: Jun. 7, 2013

(65) Prior Publication Data

US 2013/0338091 A1 Dec. 19, 2013

Related U.S. Application Data

(60) Provisional application No. 61/660,947, filed on Jun. 18, 2012.

(51) Int. Cl.
  *G01N 33/68* (2006.01)
  *C07K 16/18* (2006.01)
  *G01N 33/574* (2006.01)

(52) U.S. Cl.
  CPC ............ *G01N 33/6893* (2013.01); *C07K 16/18* (2013.01); *G01N 33/57415* (2013.01); *G01N 33/57419* (2013.01); *C07K 2317/34* (2013.01); *G01N 2800/52* (2013.01)

(58) Field of Classification Search
  CPC . G01N 33/6893; G01N 2800/52; C07K 16/18
  USPC .............................. 530/387.3, 387.9; 435/7.1
  See application file for complete search history.

(56) References Cited

FOREIGN PATENT DOCUMENTS

WO    WO 2010/145693    * 12/2010

OTHER PUBLICATIONS

Cucchiarelli et al. β-Tubulin Isotype Classes II and V Expression Patterns in Nonsmall Cell Lung Carcinomas. Cell Motil Cytoskelclon65: 675-685, 2008.*
Chao S K et al., entitled "Characterization of human βV-tubulin antibody and expression of this isotype in normal and malignant human tissue," Cytoskeleton, Aug. 2012;69(8):566-76, Abstract Only.
Banerjee A et al., entitled "Localization of betav tubulin in the cochlea and cultured cells with a novel monoclonal antibody," Cell Motil Cytoskeleton, Jun. 2008;65(6):505-14, Abstract Only.

* cited by examiner

*Primary Examiner* — Mark Shibuya
*Assistant Examiner* — Yih-Horng Shiao
(74) *Attorney, Agent, or Firm* — Amster, Rothstein & Ebenstein LLP

(57) ABSTRACT

Antibodies to human βV-tubulin, fragments thereof, and compositions comprising such are provided. Diagnostic, prognostic and identification methods employing such antibodies or fragments thereof are also provided.

9 Claims, 8 Drawing Sheets

```
humanβV  MREIVHIQAGQCGNQIGTKFWEVISDEHGIDKAGGYVGDSALQLERIAVY 50
mouseβV  MREIVHIQAGQCGNQIGTKFWEVISDEHGIDKAGGYVGDSALQLERIAVY 50 humanβV  YNESSSKKYVPRAALVDLEPGTMDSVRSGPFGQLFRPDNFIFGQTGAGNN 100
mouseβV  YNESSSRKYVPRAALVDLEPGTMDSVRSGPFGQLFRPDNFIFGQTGAGNN 100 humanβV  WAKGHYTEGAELVDSVLDVVRKECEHCDCLQGFQLTHSLGGGTGSGMGTL 150
mouseβV  WAKGHYTEGAELVDSVLDVVRKECEHCDCLQGFQLTHSLGGGTGSGMGTL 150 humanβV  LISKIREEYPDRIMNTFSVMPSPKVSDTVVEPYNATLSVHQLVENTDETY 200
mouseβV  LISKIREEYPDRIMNTFSVMPSPKVSDTVVEPYNATLSVHQLVENTDETY 200 humanβV  CIDNEALYDICFRTLKLTTPTYGDLNHLVSATMSGVTTSLRFPGQLNADL 250
mouseβV  CIDNEALYDICFRTLKLTTPTYGDLNHLVSATMSGVTTSLRFPGQLNADL 250 humanβV  RKLAVNMVPFPRLHFFMPGFAPLTARGSQQYRALTVPELTQQMFDAKNMM 300
mouseβV  RKLAVNMVPFPRLHFFMPGFAPLTSRGSQQYRALTVPELTQQMFDAKNMM 300 humanβV  AACDPRHGRYLTVATVFRGPMSMKEVDEQMLAIQSKNSSYFVEWIPNNVK 350
mouseβV  AACDPRHGRYLTVATVFRGPMSMKEVDEQMLAIQSKNSSYFVEWIPNNVK 350 humanβV  YAVCDIPPRGLKMASTFIGNSTAIQELFKRISEQFSAMFRRKAFLHWFTG 400
mouseβV  YAVCDIPPRGLKMASTFIGNSTAIQELFKRISEQFSAMFRRKAFLHWFTG 400 humanβV  EGMDEMEFTEAESNMNDLVSEYQQYQDATANDGEEAFEDEEEEI 445
mouseβV  EGMDEMEFTEAESNMNDLVSEYQQYQDATANDGEEAFEDEEEEI 443
```

Fig. 8

SEQUENCE LISTING

```
<160> NUMBER OF SEQ ID NOS: 7

<210> SEQ ID NO 1
<211> LENGTH: 14
<212> TYPE: PRT
<213> ORGANISM: Homo sapiens

<400> SEQUENCE: 1

Gly Glu Glu Ala Phe Glu Asp Glu Glu Glu Glu Ile Asp Gly
1               5                   10

<210> SEQ ID NO 2
<211> LENGTH: 15
<212> TYPE: PRT
<213> ORGANISM: Homo sapiens

<400> SEQUENCE: 2

Cys Gly Glu Glu Ala Phe Glu Asp Glu Glu Glu Glu Ile Asp Gly
1               5                   10                  15

<210> SEQ ID NO 3
<211> LENGTH: 15
<212> TYPE: PRT
<213> ORGANISM: Homo sapiens

<400> SEQUENCE: 3

Cys Tyr Glu Asp Asp Glu Glu Glu Ser Glu Ala Gln Gly Pro Lys
1               5                   10                  15

<210> SEQ ID NO 4
<211> LENGTH: 14
<212> TYPE: PRT
<213> ORGANISM: Homo sapiens

<400> SEQUENCE: 4

Tyr Glu Asp Asp Glu Glu Glu Ser Glu Ala Gln Gly Pro Lys
1               5                   10

<210> SEQ ID NO 5
<211> LENGTH: 10
<212> TYPE: PRT
<213> ORGANISM: Homo sapiens

<400> SEQUENCE: 5
```

-continued

```
Glu Glu Asp Glu Glu Glu Ile Asp Val
1               5                   10

<210> SEQ ID NO 6
<211> LENGTH: 440
<212> TYPE: PRT
<213> ORGANISM: Homo sapiens

<400> SEQUENCE: 6

Met Arg Glu Ile Val His Ile Gln Ala Gly Gln Cys Gly Asn Gln Gly
1               5                   10                  15

Thr Lys Phe Trp Glu Val Ile Ser Asp Glu His Gly Ile Asp Pro Ala
            20                  25                  30

Gly Gly Tyr Val Gly Asp Ser Ala Leu Gln Leu Glu Arg Ile Asn Val
        35                  40                  45

Tyr Tyr Asn Glu Ser Ser Gln Lys Tyr Val Pro Arg Ala Ala Leu
    50                  55                  60

Val Asp Leu Glu Pro Gly Thr Met Asp Ser Val Arg Ser Gly Pro Phe
65                  70                  75                  80

Gly Gln Leu Phe Arg Pro Asp Asn Phe Ile Phe Gly Gln Thr Gly Ala
                85                  90                  95

Gly Asn Asn Trp Ala Lys Gly His Tyr Thr Glu Gly Ala Glu Leu Val
            100                 105                 110

Asp Ala Val Leu Asp Val Val Arg Lys Glu Cys Glu His Cys Asp Cys
        115                 120                 125

Leu Gln Gly Phe Gln Leu Thr His Ser Leu Gly Gly Gly Thr Gly Ser
130                 135                 140

Gly Met Gly Thr Leu Leu Ile Ser Lys Ile Arg Glu Glu Phe Pro Asp
145                 150                 155                 160

Arg Ile Met Asn Thr Phe Ser Val Met Pro Ser Pro Lys Val Ser Asp
                165                 170                 175

Thr Val Val Glu Pro Tyr Asn Ala Thr Leu Ser Val His Gln Leu Val
            180                 185                 190

Glu Asn Thr Asp Glu Thr Tyr Cys Ile Asp Asn Glu Ala Leu Tyr Asp
        195                 200                 205

Ile Cys Phe Arg Thr Leu Lys Leu Thr Thr Pro Thr Tyr Gly Asp Leu
210                 215                 220

Asn His Leu Val Ser Ala Thr Met Ser Gly Val Thr Thr Ser Leu Arg
225                 230                 235                 240

Phe Pro Gly Gln Leu Asn Ala Asp Leu Arg Lys Leu Ala Val Asn Met
                245                 250                 255

Val Pro Phe Pro Arg Leu His Phe Phe Met Pro Gly Phe Ala Pro Leu
            260                 265                 270

Thr Ser Arg Gly Ser Gln Gln Tyr Arg Ala Leu Thr Val Pro Glu Leu
        275                 280                 285

Thr Gln Gln Met Phe Asp Ala Arg Asn Met Met Ala Ala Cys Asp Pro
290                 295                 300

Arg His Gly Arg Tyr Leu Thr Val Ala Thr Val Phe Arg Gly Pro Met
305                 310                 315                 320

Ser Met Lys Glu Val Asp Glu Gln Met Leu Ala Gln Ser Lys Asn Ser
                325                 330                 335

Ser Tyr Phe Val Glu Trp Ile Pro Asn Asn Val Lys Val Ala Val Cys
            340                 345                 350

Asp Pro Pro Arg Gly Leu Lys Met Ala Ser Thr Phe Gly Asn Ser Thr
```

```
                    355                 360                 365
Ala Gln Glu Leu Phe Lys Arg Ser Glu Gln Phe Ser Ala Met Phe Arg
            370                 375                 380

Arg Lys Ala Phe Leu His Trp Phe Thr Gly Glu Gly Met Asp Glu Met
385                 390                 395                 400

Glu Phe Thr Glu Ala Glu Ser Asn Met Asn Asp Leu Val Ser Glu Tyr
                    405                 410                 415

Gln Gln Tyr Gln Asp Ala Thr Ala Asn Asp Gly Glu Glu Ala Phe Glu
            420                 425                 430

Asp Glu Glu Glu Glu Ile Asp Gly
            435                 440

<210> SEQ ID NO 7
<211> LENGTH: 447
<212> TYPE: PRT
<213> ORGANISM: Mus musculus

<400> SEQUENCE: 7

Met Arg Glu Ile Val His Ile Gln Ala Gly Gln Cys Gly Asn Gln Ile
1               5                   10                  15

Gly Thr Lys Phe Trp Glu Val Ile Ser Asp Glu His Gly Ile Asp Gln
            20                  25                  30

Ala Gly Gly Tyr Val Gly Asp Ser Ala Leu Gln Leu Glu Arg Ile Ser
        35                  40                  45

Val Tyr Tyr Asn Glu Ser Ser Ser Lys Lys Tyr Val Pro Arg Ala Ala
    50                  55                  60

Leu Val Asp Leu Glu Pro Gly Thr Met Asp Ser Val Arg Ser Gly Pro
65                  70                  75                  80

Phe Gly Gln Leu Phe Arg Pro Asp Asn Phe Ile Phe Gly Gln Thr Gly
                85                  90                  95

Ala Gly Asn Asn Trp Ala Lys Gly His Tyr Thr Glu Gly Ala Glu Leu
            100                 105                 110

Val Asp Ser Val Leu Asp Val Val Arg Lys Glu Cys Glu His Cys Asp
        115                 120                 125

Cys Leu Gln Gly Phe Gln Leu Thr His Ser Leu Gly Gly Gly Thr Gly
    130                 135                 140

Ser Gly Met Gly Thr Leu Leu Ile Ser Lys Ile Arg Glu Glu Tyr Pro
145                 150                 155                 160

Asp Arg Ile Met Asn Thr Phe Ser Val Met Pro Ser Pro Lys Val Ser
                165                 170                 175

Asp Thr Val Val Glu Pro Tyr Asn Ala Thr Leu Ser Val His Gln Leu
            180                 185                 190

Val Glu Asn Thr Asp Glu Thr Tyr Cys Ile Asp Asn Glu Ala Leu Tyr
        195                 200                 205

Asp Ile Cys Phe Arg Thr Leu Lys Leu Thr Thr Pro Thr Tyr Gly Asp
    210                 215                 220

Leu Asn His Leu Val Ser Ala Thr Met Ser Gly Val Thr Thr Ser Leu
225                 230                 235                 240

Arg Phe Pro Gly Gln Leu Asn Ala Asp Leu Arg Lys Leu Ala Val Asn
                245                 250                 255

Met Val Pro Phe Pro Arg Leu His Phe Phe Met Pro Gly Phe Ala Pro
            260                 265                 270

Leu Thr Ala Arg Gly Ser Gln Gln Tyr Arg Ala Leu Thr Val Pro Glu
        275                 280                 285
```

-continued

```
Leu Thr Gln Gln Met Phe Asp Ala Lys Asn Met Met Ala Ala Cys Asp
    290                 295                 300

Pro Arg His Gly Arg Tyr Leu Thr Val Ala Thr Val Phe Arg Gly Pro
305                 310                 315                 320

Met Ser Met Lys Glu Val Asp Glu Gln Met Leu Ala Ile Gln Asn Lys
                325                 330                 335

Asn Ser Ser Tyr Phe Val Glu Trp Ile Pro Asn Asn Val Lys Val Ala
            340                 345                 350

Val Cys Asp Ile Pro Pro Arg Gly Leu Lys Met Ala Ser Thr Phe Ile
        355                 360                 365

Gly Asn Ser Thr Ala Ile Gln Glu Leu Phe Lys Arg Ser Glu Gln Phe
    370                 375                 380

Ser Ala Met Phe Arg Arg Lys Ala Phe Leu His Trp Phe Thr Gly Glu
385                 390                 395                 400

Gly Met Asp Glu Met Glu Phe Thr Glu Ala Glu Ser Ser Asn Met Asn
                405                 410                 415

Asp Leu Val Ser Glu Tyr Gln Gln Tyr Gln Asp Ala Thr Val Asn Asp
            420                 425                 430

Gly Glu Glu Ala Phe Glu Asp Glu Asp Glu Glu Glu Ile Asn Glu
    435                 440                 445
```

HUMAN βV-TUBULIN ANTIBODY AND METHODS OF USE

CROSS-REFERENCE TO RELATED APPLICATIONS

This application claims benefit of U.S. Provisional Application No. 61/660,947, filed Jun. 18, 2012, the contents of which are hereby incorporated by reference.

STATEMENT OF GOVERNMENT SUPPORT

This invention was made with government support under grant number CA077263 awarded by the National Institutes of Health. The government has certain rights in the invention.

BACKGROUND OF THE INVENTION

The disclosures of all publications, including as referred to herein the by number in parentheses, and the disclosures of all patents, patent application publications and books referred to in this application, are hereby incorporated by reference in their entirety into the subject application to more fully describe the art to which the subject invention pertains.

Mammals express seven distinct β-tubulin isotypes, I, II, III, IVa, IVb, V, and VI and eight α-tubulin isotypes (1-3). Heterodimers of α- and β-tubulin assemble head to tail to form protofilaments whose lateral assembly constitutes the microtubule wall. Each of the multiple α- and β-tubulin isotypes are highly conserved, and are identified primarily by their specific C-terminus sequence (2, 4). Several isotype specific antibodies have been made by designing epitopes to these unique regions (5).

Abnormal distribution and expression of α- and β-tubulin isotypes have been reported in numerous malignancies (6), and so altered tubulin isotype expression may promote a more aggressive and drug resistant tumor phenotype (7). For example, βIII-tubulin is overexpressed in ovarian, lung, prostate, and breast cancer cell lines (7, 8), and numerous studies have identified it as a prognosticator of poor survival (9, 10) while others have shown that βIII overexpression may be associated with response to microtubule interacting drugs (11, 12). Furthermore, βIII-tubulin overexpression is associated with cell-based models of acquired Taxol (paclitaxel) resistance (7, 11, 12), and more recently resistance to DNA-damaging drugs (13). Most of the evidence that has led to the association between βIII-tubulin expression and poor survival were derived from immunohistochemistry using βIII-tubulin specific antibodies (9, 12, 14). Therefore, studies addressing the distribution and expression of the various tubulin isotypes in normal and malignant tissue are limited by availability and specificity of antibodies. For this reason, little is known about the expression of α-tubulin isotypes or some of the less well-characterized β-tubulin isotypes, such as βV. A mouse βV-antibody has been developed and well characterized (5), however due to the specificity of the antibody it cannot be used to detect human βV-tubulin.

βV-tubulin mRNA has been detected in most human tissue types using qRT-PCR15 and it has been proposed that it is required for progression through mitosis (16). It has also been suggested that βV-tubulin overexpression mediates Taxol-dependence (17), a characteristic of some Taxol-resistant cells that require small quantities of drug for normal growth in tissue culture (18). Overexpression of βV-tubulin in Chinese hamster ovary (CHO) cells has been shown to contribute to the dependence of these cells on Taxol for growth (19). Therefore, βV tubulin expression may be an important marker for defective microtubule stabilization associated with cellular transformation, or drug resistance.

The present invention addresses the need for a specific antibody for human βV-tubulin, and also provides diagnostic, prognostic and identification methods of use based thereon.

SUMMARY OF THE INVENTION

This invention provides an isolated antibody directed against human βV-tubulin.

This invention also provides an isolated human βV-tubulin-binding fragment of an antibody directed against human βV-tubulin.

This invention also provides a method for determining the taxane-sensitivity of a tumor in a subject comprising contacting a sample of the tumor obtained from the subject with an agent that binds to human βV-tubulin, quantitating the amount of agent bound, and comparing the amount of bound agent to a predetermined control amount, and determining the taxane-sensitivity of the tumor, wherein an amount of agent bound in excess of the predetermined control amount indicates that the tumor is taxane-insensitive, and an amount of agent bound below the predetermined control amount indicates that the tumor is taxane-sensitive.

This invention also provides a method for determining whether a sample from a subject is cancerous, comprising contacting the sample with an agent that binds to human βV-tubulin, quantitating the amount of agent bound, and comparing the amount of bound agent to a predetermined control amount, and determining whether the sample is cancerous, wherein an amount of agent bound in excess of the predetermined control amount indicates that the tumor is cancerous, and an amount of agent bound below the predetermined control amount indicates that the tumor is not cancerous.

This invention also provides a method for determining whether a sample from a subject is cancerous, comprising contacting the sample with an agent that binds to human βV-tubulin, quantitating the amount of agent bound, and comparing the amount of bound agent to a predetermined control amount, and determining whether the sample is cancerous, wherein an amount of agent bound in excess of the predetermined control amount indicates that the tumor is not cancerous, and an amount of agent bound below the predetermined control amount indicates that the tumor is cancerous.

This invention also provides a method for determining the prognosis of a cancer in a subject, comprising contacting the sample with an agent that binds to human βV-tubulin, quantitating the amount of agent bound, and comparing the amount of bound agent to a predetermined control amount, and determining whether the sample is cancerous and thereby determining the prognosis, wherein an amount of agent bound in excess of the predetermined control amount indicates a poor prognosis, and an amount of agent bound below the predetermined control amount indicates a good prognosis.

Additional objects of the invention will be apparent from the description which follows.

BRIEF DESCRIPTION OF THE DRAWINGS

FIG. 8. Sequence alignment of human (SEQ ID NO:6) and mouse βV-tubulin (SEQ ID NO:7).

DETAILED DESCRIPTION OF THE INVENTION

Figures 1A, 1B, 1C:
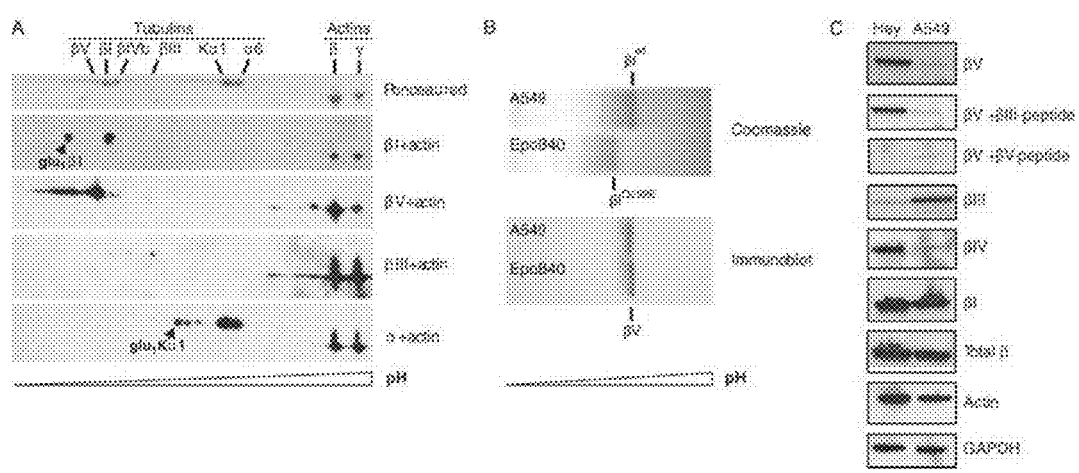
FIG. 1A-1C. Isotype-specific immunoreactivity of a human βV-tubulin antibody A) Taxol-pelleted microtubules from Hey cells were resolved by isoelectric focusing IPG strips at pH 4.5-5.5, followed by SDS-PAGE, total protein staining and immunoblotting with isotype specific antibodies as indicated. B) Isoelectric focusing of wild type and mutant βI-tubulin in A549 and A549.EpoB40, respectively. IEF gels were either stained with Coomassie blue (top), or electrotransfered onto nitrocellulose for immunoblotting with anti human βV-tubulin antibody (bottom). C) Pre-incubation of antibodies with βIII- or βV-tubulin C-terminal peptides and subsequent immunoblotting using the βV-tubulin antibody on Hey and A549 cell lysates. Also shown are immunoblots with the indicated isotype specific antibodies for βV-, βIII-, βI-, and total β-tubulin.

This invention provides an isolated antibody directed against human βV-tubulin.

In an embodiment, the antibody is directed against an epitope comprising GEEAFEDEEEEIDG (SEQ ID NO:1). In an embodiment, the antibody is directed against an epitope comprising CGEEAFEDEEEEIDG (SEQ ID NO:2). In an embodiment, the antibody does not bind human βIII-tubulin. In an embodiment, the antibody does not bind a protein comprising YEDDEEESEAQGPK (SEQ ID NO:4) or a protein comprising CYEDDEEESEAQGPK (SEQ ID NO:3). In an embodiment, the antibody does not bind human βI-tubulin. In an embodiment, the antibody does not bind mouse βV-tubulin. In an embodiment, the antibody does not bind human N-Myc oncoprotein. In an embodiment, the antibody is a polyclonal antibody. In an embodiment, the antibody is a monoclonal antibody. In an embodiment, the antibody is a human antibody, a humanized antibody or a chimeric antibody. This invention also provides an isolated human βV-tubulin-binding fragment of any of the antibodies described herein. In an embodiment, the fragment comprises an Fab, an Fab', an F(ab')2, an Fd, an Fv, a complementarity determining region (CDR), or a single-chain antibody (scFv).

This invention also provides a method for determining the taxane-sensitivity of a tumor in a subject comprising contacting a sample of the tumor obtained from the subject with an agent that binds to human βV-tubulin, quantitating the amount of agent bound, and comparing the amount of bound agent to a predetermined control amount, and determining the taxane-sensitivity of the tumor, wherein an amount of agent bound in excess of the predetermined control amount indicates that the tumor is taxane-insensitive, and an amount of agent bound below the predetermined control amount indicates that the tumor is taxane-sensitive.

In an embodiment, the taxane is paclitaxel or docetaxel. In an embodiment, the method further comprises treating the subject with an anti-tumor medication, wherein the subject is treated with a taxane if determined to have a taxane-sensitive tumor, and wherein the subject is treated with a non-taxane medication if the subject is determined to have a taxane-insensitive tumor. In an embodiment, the non-taxane medication is an anthracycline chemotherapy. In an embodiment, the anthracycline chemotherapy comprises daunorubicin, daunorubicin, doxorubicin, epirubicin, idarubicin or valrubicin.

This invention also provides a method for determining whether a sample from a subject is cancerous, comprising contacting the sample with an agent that binds to human βV-tubulin, quantitating the amount of agent bound, and comparing the amount of bound agent to a predetermined control amount, and determining whether the sample is cancerous, wherein an amount of agent bound in excess of the predetermined control amount indicates that the tumor is cancerous, and an amount of agent bound below the predetermined control amount indicates that the tumor is not cancerous. In an embodiment, the sample is a breast, lung or ovary sample, or comprises an intratubular cell. In an embodiment, the method further comprises treating the subject with an anti-cancer medication wherein the subject is determined to have a cancerous tumor. In an embodiment, the anti-cancer medication is a chemotherapy or radiotherapy.

This invention also provides a method for determining whether a sample from a subject is cancerous, comprising contacting the sample with an agent that binds to human βV-tubulin, quantitating the amount of agent bound, and comparing the amount of bound agent to a predetermined control amount, and determining whether the sample is cancerous, wherein an amount of agent bound in excess of the predetermined control amount indicates that the tumor is not cancerous, and an amount of agent bound below the predetermined control amount indicates that the tumor is cancerous. In an embodiment, the sample is a prostate sample. In an embodiment, the method further comprises treating the subject with an anti-cancer medication wherein the subject is determined to have a cancerous tumor. In an embodiment, the anti-cancer medication is a chemotherapy or radiotherapy.

This invention also provides a method for determining the prognosis of a cancer in a subject, comprising contacting the sample with an agent that binds to human βV-tubulin, quantitating the amount of agent bound, and comparing the amount of bound agent to a predetermined control amount, and determining whether the sample is cancerous and thereby determining the prognosis, wherein an amount of agent bound in excess of the predetermined control amount indicates a poor prognosis, and an amount of agent bound below the predetermined control amount indicates a good prognosis.

In an embodiment of the methods described herein, the agent is an antibody is directed against an epitope comprising GEEAFEDEEEEIDG (SEQ ID NO:1). In an embodiment of the methods described herein, the antibody does not bind human βIII-tubulin. In an embodiment of the methods described herein, the antibody does not bind a protein comprising YEDDEEESEAQGPK (SEQ ID NO:4) or a protein comprising CYEDDEEESEAQGPK (SEQ ID NO:3). In an embodiment of the methods described herein, the antibody does not bind human βI-tubulin. In an embodiment of the methods described herein, the antibody does not bind mouse βV-tubulin. In an embodiment of the methods described herein, the antibody does not bind human N-Myc oncoprotein. In an embodiment of the methods described herein, the antibody is a polyclonal antibody. In an embodiment of the methods described herein, the antibody is a monoclonal antibody. In an embodiment of the methods described herein, the antibody is a human antibody, a humanized antibody or a chimeric antibody. In an embodiment of the methods described herein, the agent is an isolated human βV-tubulin-binding fragment of any of the antibodies described herein. In an embodiment, the fragment comprises an Fab, an Fab', an F(ab')2, an Fd, an Fv, a complementarity determining region (CDR), or a single-chain antibody (scFv).

In an embodiment of the methods, the agent, for example the antibody or fragment, is labeled with a detectable marker. Detectable markers are well known in the art an include, in non-limiting examples, fluorescent dyes, radioisotopes, radio-opaque molecules.

In an embodiment of the methods, the methods further comprise obtaining a sample from the subject.

Cancers or tumors of the methods of the invention include of the breast, nasopharynx, pharynx, lung, bone, brain, sialaden, stomach, esophagus, testes, ovary, uterus, endometrium, liver, small intestine, appendix, colon, rectum, gall bladder, pancreas, kidney, urinary bladder, breast, cervix, vagina, vulva, prostate, thyroid or skin, or is a glioma.

As used herein, the term "antibody" refers to an intact antibody, i.e. with complete Fc and Fv regions. "Fragment" refers to any portion of an antibody, or portions of an antibody linked together, such as a single-chain Fv (scFv), which is less than the whole antibody but which is an antigen-binding portion and which competes with the intact antibody of which it is a fragment for specific binding. As such a fragment can be prepared, for example, by cleaving an intact antibody or by recombinant means. See generally, Fundamental Immunology, Ch. 7 (Paul, W., ed., 2nd ed. Raven Press, N.Y. (1989), hereby incorporated by reference in its entirety). Antigen-binding fragments may be produced by recombinant DNA techniques or by enzymatic or chemical cleavage of intact antibodies or by molecular biology techniques. In some embodiments, a fragment is an Fab, Fab', F(ab')$_2$, F$_d$, F$_v$, complementarity determining region (CDR) fragment, single-chain antibody (scFv), (a variable domain light chain (V$_L$) and a variable domain heavy chain (V$_H$) linked via a peptide linker. In an embodiment the linker of the scFv is 10-25 amino acids in length. In an embodiment the peptide linker comprises glycine, serine and/or threonine residues. For example, see Bird et al., Science, 242: 423-426 (1988) and Huston et al., Proc. Natl. Acad. Sci. USA, 85:5879-5883 (1988) each of which are hereby incorporated by reference in their entirety), or a polypeptide that contains at least a portion of an antibody that is sufficient to confer human βV-tubulin-specific antigen binding on the polypeptide, including a diabody. From N-terminus to C-terminus, both the mature light and heavy chain variable domains comprise the regions FR1, CDR1, FR2, CDR2, FR3, CDR3 and FR4. The assignment of amino acids to each domain is in accordance with the definitions of Kabat, Sequences of Proteins of Immunological Interest (National Institutes of Health, Bethesda, Md. (1987 and 1991)), Chothia & Lesk, J. Mol. Biol. 196:901-917 (1987), or Chothia et al., Nature 342:878-883 (1989), each of which are hereby incorporated by reference in their entirety). As used herein, the term "polypeptide" encompasses native or artificial proteins, protein fragments and polypeptide analogs of a protein sequence. A polypeptide may be monomeric or polymeric. As used herein, an F$_d$ fragment means an antibody fragment that consists of the V$_H$ and CH1 domains; an F$_v$ fragment consists of the V$_L$ and V$_H$ domains of a single arm of an antibody; and a dAb fragment (Ward et al., Nature 341:544-546 (1989) hereby incorporated by reference in its entirety) consists of a V$_H$ domain.

In some embodiments, fragments are at least 5, 6, 8 or 10 amino acids long. In other embodiments, the fragments are at least 14, at least 20, at least 50, or at least 70, 80, 90, 100, 150 or 200 amino acids long.

The term "monoclonal antibody" is not intended to be limited as regards to the source of the antibody or the manner in which it is made (e.g., by hybridoma, phage selection, recombinant expression, transgenic animals, etc.). The term "monoclonal antibody" as used herein refers to an antibody member of a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins. Thus an identified monoclonal antibody can be produced by non-hybridoma techniques, e.g. by appropriate recombinant means once the sequence thereof is identified.

As used herein, the terms "isolated antibody" refers to an antibody that by virtue of its origin or source of derivation has one to five of the following: (1) is not associated with naturally associated components that accompany it in its native state, (2) is free of other proteins from the same species, (3) is expressed by a cell from a different species, (4) does not occur in nater, (5) is created through the hand of man.

The invention provides a composition or pharmaceutical composition comprising an isolated antibody directed against human βV-tubulin, or a fragment thereof. In an embodiment the composition or pharmaceutical composition comprising one or more of the antibodies or fragments described herein is substantially pure with regard to the antibody or fragment. A composition or pharmaceutical composition comprising one or more of the antibodies or fragments described herein is "substantially pure" with regard to the antibody or fragment when at least about 60 to 75% of a sample of the composition or pharmaceutical composition exhibits a single species of the antibody or fragment. A substantially pure composition or pharmaceutical composition comprising one or more of the antibodies or fragments described herein can comprise, in the portion thereof which is the antibody or fragment, 60%, 70%, 80% or 90% of the antibody or fragment of the single species, more usually about 95%, and preferably over 99%. Antibody purity or homogeneity may tested by a number of means well known in the art, such as polyacrylamide gel electrophoresis or HPLC. The compositions can comprise a carrier, including a pharmaceutically acceptable carrier.

As used herein, a "human antibody" unless otherwise indicated is one whose sequences correspond to (i.e. are identical in sequence to) an antibody that could be produced by a human and/or has been made using any of the techniques for making human antibodies as disclosed herein but not one that has been produced in a human. This definition of a human antibody specifically excludes a humanized antibody. A "human antibody" as used herein can be produced using various techniques known in the art, including phage-display libraries (e.g. Hoogenboom and Winter, J. Mol. Biol., 227: 381 (1991); Marks et al., J. Mol. Biol., 222:581 (1991), hereby incorporated by reference in its entirety), by methods described in Cole et al., Monoclonal Antibodies and Cancer Therapy, Alan R. Liss, p. 77 (1985) (hereby incorporated by reference in its entirety); Boerner et al., J. Immunol., 147(1): 86-95 (1991) (hereby incorporated by reference in its entirety), van Dijk and van de Winkel, Curr. Opin. Pharmacol., 5: 368-74 (2001) (hereby incorporated by reference in its entirety), and by administering the antigen (e.g. human βV-tubulin or a C-terminal fragment thereof) to a transgenic animal that has been modified to produce such antibodies in response to antigenic challenge, but whose endogenous loci have been disabled, e.g., immunized xenomice (see, e.g., U.S. Pat. Nos. 5,939,598; 6,075,181; 6,114,598; 6,150,584 and 6,162,963 to Kucherlapati et al. regarding XENOMOUSE™ technology, each of which patents are hereby incorporated by reference in their entirety), e.g. VelocImmune® (Regeneron, Tarrytown, N.Y.), e.g. UltiMab® platform (Medarex, now Bristol Myers Squibb, Princeton, N.J.). See also, for example, Li et al., Proc. Natl. Acad. Sci. USA, 103:3557-3562 (2006) regarding human antibodies generated via a human B-cell hybridoma technology. See also KM Mouse® system, described in PCT Publication WO 02/43478 by Ishida et al., in which the mouse carries a human heavy chain transchromosome and a human light chain transgene, and the TC mouse system, described in Tomizuka et al. (2000) Proc. Natl. Acad. Sci. USA 97:722-727, in which the mouse carries both a human heavy chain transchromosome and a human light chain transchromosome, both of which are hereby incorporated by reference in their entirety. In each of these systems, the transgenes and/or transchromosomes carried by the mice comprise human immunoglobulin variable and constant region sequences.

The term "human antibody", as used herein, is intended to include antibodies having variable regions in which both the framework and CDR regions are sequences of human origin or identical thereto. Furthermore, if the antibody (e.g. an intact antibody rather than, for example, an Fab fragment) contains a constant region, the constant region also is derived from such human sequences, e.g., human germline sequences, or mutated versions of human germline sequences. The human antibodies of the invention may include amino acid residues not encoded by human sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. In one non-limiting embodiment, where the human antibodies are human monoclonal antibodies, such antibodies can be produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a hypervariable region (HVR) of the recipient are replaced by residues from a HVR of a non-human species (donor antibody) such as mouse, rat, rabbit, or nonhuman primate having the desired specificity, affinity, and/or capacity. In some instances, FR residues of the human immunoglobulin variable domain are replaced by corresponding non-human residues. These modifications may be made to further refine antibody performance. Furthermore, in a specific embodiment, humanized antibodies may comprise residues that are not found in the recipient antibody or in the donor antibody. In an embodiment, the humanized antibodies do not comprise residues that are not found in the recipient antibody or in the donor antibody. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. See, e.g., Jones et al., *Nature* 321:522-525 (1986); Riechmann et al., *Nature* 332:323-329 (1988); Presta, Curr. Op. Struct. Biol. 2:593-596 (1992); Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409, the contents of each of which references and patents are hereby incorporated by reference in their entirety. In one embodiment where the humanized antibodies do comprise residues that are not found in the recipient antibody or in the donor antibody, the Fc regions of the antibodies are modified as described in WO 99/58572, the content of which is hereby incorporated by reference in its entirety.

Techniques to humanize a monoclonal antibody are described in U.S. Pat. Nos. 4,816,567; 5,807,715; 5,866,692; 6,331,415; 5,530,101; 5,693,761; 5,693,762; 5,585,089; and 6,180,370, the content of each of which is hereby incorporated by reference in its entirety.

A number of "humanized" antibody molecules comprising an antigen-binding site derived from a non-human immunoglobulin have been described, including antibodies having rodent or modified rodent V regions and their associated complementarity determining regions (CDRs) fused to human constant domains. See, for example, Winter et al. Nature 349: 293-299 (1991), Lobuglio et al. Proc. Nat. Acad. Sci. USA 86: 4220-4224 (1989), Shaw et al. J. Immunol. 138: 4534-4538 (1987), and Brown et al. Cancer Res. 47: 3577-3583 (1987), the content of each of which is hereby incorporated by reference in its entirety. Other references describe rodent hypervariable regions or CDRs grafted into a human supporting framework region (FR) prior to fusion with an appropriate human antibody constant domain. See, for example, Riechmann et al. Nature 332: 323-327 (1988), Verhoeyen et al. Science 239: 1534-1536 (1988), and Jones et al. Nature 321: 522-525 (1986), the content of each of which is hereby incorporated by reference in its entirety. Another reference describes rodent CDRs supported by recombinantly veneered rodent framework regions—European Patent Publication No. 0519596 (incorporated by reference in its entirety). These "humanized" molecules are designed to minimize unwanted immunological response toward rodent anti-human antibody molecules which limits the duration and effectiveness of therapeutic applications of those moieties in human recipients. The antibody constant region can be engineered such that it is immunologically inert (e.g., does not trigger complement lysis). See, e.g. PCT Publication No. WO99/58572; UK Patent Application No. 9809951.8. Other methods of humanizing antibodies that may also be utilized are disclosed by Daugherty et al., Nucl. Acids Res. 19: 2471-2476 (1991) and in U.S. Pat. Nos. 6,180,377; 6,054,297; 5,997,867; 5,866,692; 6,210,671; and 6,350,861; and in PCT Publication No. WO 01/27160 (each incorporated by reference in their entirety).

Other forms of humanized antibodies have one or more CDRs (CDR L1, CDR L2, CDR L3, CDR H1, CDR H2, or CDR H3) which are altered with respect to the original antibody, which are also termed one or more CDRs "derived from" one or more CDRs from the original antibody.

In embodiments, the antibodies or fragments herein can be produced recombinantly, for example antibodies expressed using a recombinant expression vector transfected into a host cell, antibodies isolated from a recombinant, combinatorial human antibody library, antibodies isolated from an animal (e.g., a mouse) that is transgenic for human immunoglobulin genes.

In an embodiment, the antibodies or antibody fragments of the invention specifically bind to human βV-tubulin. As used herein, the terms "is capable of specifically binding", "specifically binds", or "preferentially binds" refers to the property of an antibody or fragment of binding to the (specified) antigen with a dissociation constant that is <1 µM, preferably <1 nM and most preferably <10 pM. In an embodiment, the $K_d$ of the antibody for human βV-tubulin or a C-terminal fragment thereof is 250-500 µM. An epitope that "specifically binds", or "preferentially binds" (used interchangeably herein) to an antibody or a polypeptide is a term well understood in the art, and methods to determine such specific or preferential binding are also well known in the art. A molecular entity is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a human βV-tubulin conformational epitope is an antibody that binds this epitope with greater affinity, avidity, more readily, and/or with greater duration than it binds to other human β-tubulins, or non-human βV-tubulin. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding.

The term "compete", as used herein with regard to an antibody, means that a first antibody, or an antigen-binding portion thereof, binds to an epitope in a manner sufficiently similar to the binding of a second antibody, or an antigen-binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

Depending on the amino acid sequences of the constant domains of their heavy chains, antibodies (immunoglobulins) can be assigned to different classes. The antibody or fragment can be, e.g., any of an IgG, IgD, IgE, IgA or IgM antibody or fragment thereof, respectively. In an embodiment the antibody is an immunoglobulin G. In an embodiment the antibody fragment is a fragment of an immunoglobulin G. In an embodiment the antibody is an IgG1, IgG2, IgG2a, IgG2b, IgG3 or IgG4. In an embodiment the antibody comprises sequences from a human IgG1, human IgG2, human IgG2a, human IgG2b, human IgG3 or human IgG4. A combination of any of these antibodies subtypes can also be used. One consideration in selecting the type of antibody to be used is the desired serum half-life of the antibody. For example, an IgG generally has a serum half-life of 23 days, IgA 6 days, IgM 5 days, IgD 3 days, and IgE 2 days. (Abbas A K, Lichtman A H, Pober J S. Cellular and Molecular Immunology, 4th edition, W.B. Saunders Co., Philadelphia, 2000, hereby incorporated by reference in its entirety).

In an embodiment the antibody or fragment neutralizes human βV-tubulin when bound thereto. In an embodiment the antibody or fragment does not neutralize human βV-tubulin when bound thereto.

The "variable region" or "variable domain" of an antibody refers to the amino-terminal domains of the heavy or light chain of the antibody. The variable domain of the heavy chain may be referred to as "$V_H$." The variable domain of the light chain may be referred to as "$V_L$." These domains are generally the most variable parts of an antibody and contain the antigen-binding sites. The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any vertebrate species can be assigned to one of two clearly distinct types, called kappa (K) and lambda (4 based on the amino acid sequences of their constant domains.

"Framework" or "FR" residues are those variable domain residues other than the HVR residues as herein defined.

The term "hypervariable region" or "HVR" when used herein refers to the regions of an antibody variable domain which are hypervariable in sequence and/or form structurally defined loops. Generally, antibodies comprise six HVRs; three in the $V_H$ (H1, H2, H3) and three in the $V_L$ (L1, L2, L3). In native antibodies, H3 and L3 display the most diversity of the six HVRs, and H3 in particular is believed to play a unique role in conferring fine specificity to antibodies. See, e.g., Xu et al., Immunity 13:37-45 (2000); Johnson and Wu, in Methods in Molecular Biology 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., Nature 363:446-448 (1993); Sheriff et al., Nature Struct. Biol. 3:733-736 (1996). A number of HVR delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991) hereby incorporated by reference in its entirety). Chothia refers instead to the location of the structural loops (Chothia and Lesk, J. Mol. Biol. 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the $V_H$. The variable domain residues are numbered according to Kabat et al., supra, for each of these definitions.

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine of the Fc region may be removed, for example, during production or purification of the antibody, or by recombinantly engineering the nucleic acid encoding a heavy chain of the antibody. Accordingly, an intact antibody as used herein may be an antibody with or without the otherwise C-terminal cysteine.

As used herein a "conformational epitope" of human βV-tubulin, or a C-terminal fragment thereof, is an epitope formed by a plurality of amino acids, at least two of which are discontinuous, arranged in a three-dimensional formation due to the native folding of the antigen. The conformational epitope is recognized by the antigen-binding portion of an antibody directed to the conformational epitope. In an embodiment, the antibody or antigen-binding fragment thereof, of the invention binds to a conformational epitope comprising one or more residues of a protein comprising GEEAFEDEEEEIDG (SEQ ID NO:1). In an embodiment, the antibody or antigen-binding fragment thereof, of the invention binds to a conformational epitope comprising one or more residues of GEEAFEDEEEEIDG (SEQ ID NO:1). In an embodiment, the antibody or antigen-binding fragment thereof, of the invention binds to an epitope comprising at least the terminal two amino acid residues of the C-terminal carboxyl.

In an embodiment, the antibody or antigen-binding fragment thereof, of the invention binds to a linear epitope. In an embodiment, the antibody or antigen-binding fragment thereof, of the invention binds to a linear epitope comprising SEQ ID NO:1.

Compositions or pharmaceutical compositions comprising the antibodies, ScFvs or fragments of antibodies disclosed herein are preferably comprise stabilizers to prevent loss of activity or structural integrity of the protein due to the effects of denaturation, oxidation or aggregation over a period of time during storage and transportation prior to use. The compositions or pharmaceutical compositions can comprise one or more of any combination of salts, surfactants, pH and tonicity agents such as sugars can contribute to overcoming aggregation problems. Where a composition or pharmaceutical composition of the present invention is used as an injection, it is desirable to have a pH value in an approximately neutral pH range, it is also advantageous to minimize surfactant levels to avoid bubbles in the formulation which are detrimental for injection into subjects. In an embodiment, the composition or pharmaceutical composition is in liquid form and stably supports high concentrations of bioactive antibody in solution and is suitable for parenteral administration, including intravenous, intramuscular, intraperitoneal, intradermal and/or subcutaneous injection. In an embodiment, the composition or pharmaceutical composition is in liquid form and has minimized risk of bubble formation and anaphylactoid side effects. In an embodiment, the composition or pharmaceutical composition is isotonic. In an embodiment, the composition or pharmaceutical composition has a pH or 6.8 to 7.4.

In an embodiment the ScFvs or fragments of antibodies disclosed herein are lyophilized and/or freeze dried and are reconstituted for use.

Examples of pharmaceutically acceptable carriers include, but are not limited to, phosphate buffered saline solution, sterile water (including water for injection USP), emulsions such as oil/water emulsion, and various types of wetting agents. Preferred diluents for aerosol or parenteral administration are phosphate buffered saline or normal (0.9%) saline, for example 0.9% sodium chloride solution, USP. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000, the content of each of which is hereby incorporated in its entirety). In non-limiting examples, the can comprise one or more of dibasic sodium phosphate, potassium chloride, monobasic potassium phosphate, polysorbate 80 (e.g. 2-[2-[3,5-bis(2-hydroxyethoxy)oxolan-2-yl]-2-(2-hydroxyethoxy)ethoxy]ethyl (E)-octadec-9-enoate), disodium edetate dehydrate, sucrose, monobasic sodium phosphate monohydrate, and dibasic sodium phosphate dihydrate.

The antibodies, or fragments of antibodies, or compositions, or pharmaceutical compositions described herein can also be lyophilized or provided in any suitable forms including, but not limited to, injectable solutions or inhalable solutions, gel forms and tablet forms.

The term "$K_d$", as used herein, is intended to refer to the dissociation constant of an antibody-antigen interaction. One way of determining the $K_d$ or binding affinity of antibodies to human βV-tubulin or a C-terminal fragment thereof is by measuring binding affinity of monofunctional Fab fragments of the antibody. (The affinity constant is the inverted dissociation constant). To obtain monofunctional Fab fragments, an antibody (for example, IgG) can be cleaved with papain or expressed recombinantly. The affinity of an anti-human βV-tubulin Fab fragment of an antibody can be determined by surface plasmon resonance (BIAcore3000™ surface plasmon resonance (SPR) system, BIAcore Inc., Piscataway N.J.). CM5 chips can be activated with N-ethyl-N'-(3-dimethylaminopropyl)-carbodiimide hydrochloride (EDC) and N-hydroxysuccinimide (NHS) according to the supplier's instructions. Human βV-tubulin can be diluted into 10 mM sodium acetate pH 4.0 and injected over the activated chip at a concentration of 0.005 mg/mL. Using variable flow time across the individual chip channels, two ranges of antigen density can be achieved: 100-200 response units (RU) for detailed kinetic studies and 500-600 RU for screening assays. Serial dilutions (0.1-10× estimated $K_d$) of purified Fab samples are injected for 1 min at 100 microliters/min and dissociation times of up to 2 h are allowed. The concentrations of the Fab proteins are determined by ELISA and/or SDS-PAGE electrophoresis using a Fab of known concentration (as determined by amino acid analysis) as a standard. Kinetic association rates ($k_{on}$) and dissociation rates ($k_{off}$) are obtained simultaneously by fitting the data to a 1:1 Langmuir binding model (Karlsson, R. Roos, H. Fagerstam, L. Petersson, B. (1994). Methods Enzymology 6. 99-110, the content of which is hereby incorporated in its entirety) using the BIA evaluation program. Equilibrium dissociation constant ($K_d$) values are calculated as $k_{off}/k_{on}$. This protocol is suitable for use in determining binding affinity of an antibody or fragment to any human βV-tubulin. Other protocols known in the art may also be used. For example, ELISA of human βV-tubulin, or a C-terminal fragment thereof, with mAb can be used to determine the $k_D$ values. The $K_d$ values reported herein used this ELISA-based protocol.

The invention provides a method of treating a subject having a human βV-tubulin-associated pathology comprising administering to the subject an amount of a human βV-tubulin antibody effective to treat a human βV-tubulin-associated pathology. As used herein, the term "subject" for purposes of treatment includes any subject, and preferably is a subject who is in need of the treatment of the targeted pathologic condition, for example an human βV-tubulin-associated pathology. For purposes of prevention, the subject is any subject, and preferably is a subject that is at risk for, or is predisposed to, developing the targeted pathologic condition for example human βV-tubulin-associated pathology. Examples of subjects include mammals, e.g., humans, dogs, cows, horses, pigs, sheep, goats, cats, mice, rabbits, rats, and transgenic non-human animals. In specific embodiments of the invention, the subject is a human.

As used herein, a predetermined control amount is a value decided for a control. The concept of a control is well-established in the field, and can be determined, in a non-limiting example, empirically from non-afflicted subjects or samples (versus afflicted subjects or samples), and may be normalized as desired to negate the effect of one or more variables.

The invention also encompasses a nucleic acid encoding any of the antibodies or fragments thereof described herein. In an embodiment, the nucleic acid is a DNA or RNA.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

Experimental Details

Materials and Methods

Tubulin peptides and antibodies: The peptides CGEE-AFEDEEEEIDG (SEQ ID NO:2) and CYED-DEEESEAQGPK (SEQ ID NO:3) corresponding to human αV- and βIII-tubulin C-terminal sequences, respectively, were custom-synthesized by the Laboratory for Molecular Analysis at Einstein College. The cysteine residue at the N-terminus of each peptide was introduced for conjugation of peptides to maleimide-activated keyhole limpet hemocyanin (KLH), or maleimide-activated bovine serum albumin (BSA) (Pierce). Rabbits were immunized with βV-tubulin peptide-KLH conjugates by Covance Immunology Services to produce sera containing a rabbit polyclonal βV-specific antibody. Bleeds from naïve and immunized rabbits were analyzed by ELISA using βV- or βIII-tubulin peptide-BSA conjugates. Sera from the first bleed were used in all experiments. Other antibodies used were rodent βV-tubulin (5), (SHM.12G11, a gift from Dr. Ludueña, UHSC, San Antonio), βIII-tubulin (TUJ1 antibody, SDL.3D10, Sigma), βI-tubulin (SAP.4G5, Sigma), βIV-tubulin (ONS.1A6, Sigma), total β-tubulin (DM1B, Sigma), Kα1-tubulin (4D1, Sigma), actin (AC-40, Sigma), insulin (Dako), glucagon (Dako) and GAPDH (Invitrogen).

Taxol pelleted microtubules and Immunoblotting: A549 human lung cancer and Hey human ovarian cancer cells from ten 100 mm tissue culture dishes (Corning), at approximately 80-90% confluency, were harvested and Taxol pelleted microtubules were prepared for 2D gel electrophoresis as described previously (3). Microtubule pellets (containing approximately 100-200 μg of protein) were resuspended in 350 μL of solubilization buffer (7 M urea, 2 M thiourea, 4% CHAPS, 0.5% Triton X-100, 0.5% ampholyte-containing buffer pH 4.5-5.5, 20 mM DTT, and bromophenol blue), and loaded onto 24 cm IPG strips with a linear gradient of pH 4.5-5.5 (Amersham). The IPG strips were loaded onto Tris-HCl 10% acrylamidecriterion gels (Biorad) and run at 200 Volts.

Immunoblots were probed with βV-tubulin rabbit polyclonal antibody at 1:20,000 dilution in 3% milk Tris buffered saline containing 0.05% Tween 20.

Tissue Culture and Cell Lines: All cell lines were purchased from ATCC and grown in RPMI (Gibco) supplemented with 10% Australian FBS (Gibco) at 37° C., in a 5% humidified $CO_2$ atmosphere. Mouse embryonic fibroblast cells were generated in our laboratory using standard protocols.

Immunohistochemistry of paraffin embedded sections: Asynchronous cells were fixed in 4% methanol-free formaldehyde, pelleted and resuspended in matrigel. The solidified matrigel cassettes were submerged in 10% neutral buffered formalin and paraffin embedded sections were prepared by the Pathology Core at Albert Einstein College of Medicine. Re-hydrated slides were blocked for 1 h at room temperature in 5% donkey serum, 2% BSA. Antibody against βV-tubulin was used at 1:1000 in blocking solution and incubated overnight at 4° C. in a humidified chamber. Standard washing and labeling with secondary antibodies were performed. Slides were developed with DAB for 45 seconds, washed for 3 minutes with running tap water and counterstained with hematoxylin and mounted.

Human archived tissue that was formalin fixed and paraffin embedded was processed using the same protocol. These sections were left over from standard of care, and as such were exempt from institutional review board approval. The intensity and the percentage of cells positive for βV-tubulin expression were evaluated using the semi-quantitative H-score, which multiplies the percentage of cells staining positively by staining intensity (scored from 0 to 3).

Immunofluorescence: HeLa cells were seeded onto Poly-D-lysine coated chamber slides, and after overnight growth, fixed in 3.7% formaldehyde in 1×PBS for 5 min (Polysciences). Cells were permeabilized with 0.1% Triton X-100 in 1×PBS for 3 minutes and slides were blocked in 1% goat serum and 3% BSA in 1×PBS for 30 minutes at room temperature, followed by incubation with the βV-tubulin antibody at a 1:1000 dilution in blocking buffer for 1 h at room temperature. Slides were incubated with goat-anti-mouse alexa 555 and goat-anti-rabbit alexa 488 secondary antibodies (Molecular Probes) for 45 min, and mounted using Prolong Gold anti-fade with DAPI (Molecular Probes).

Results

Specificity of a human βV-tubulin polyclonal antibody: In previous studies the ability of narrow-range isoelectric focusing to resolve tubulin isotypes differing in isoelectric point (pI) by as little as 0.01 (4) has been demonstrated. Subsequent mass spectrometry of excised bands has validated the identity of these isotypes. In addition, SILAC, IEF and MS were combined to quantify relative differences in βIII- and βV-tubulin levels of expression in human cancer cell lines (20-22). These previous studies indicated that βV-tubulin was approximately three to four-fold more abundant in Hey ovarian carcinoma cells compared to human A549 lung cancer cells. To test the specificity of the βV-tubulin antibody in this study, two-dimensional (2D) immunoblots of Taxol-pelleted microtubules were carried out. Microtubules from Hey and A549 cells were used as sources of high and low βV-tubulin content, respectively (20). These 2D immunoblots were probed with antibodies specific for Kα1-, βI-, βIII-tubulins, and the βV-tubulin-specific antibody described in the present study. In order to clearly position βIII-tubulin spots, microtubules from A549 cells that expressed detectable levels of βIII-tubulin were used. Consistent with high expression in Hey cells, the anti βV-tubulin antibody strongly stained a major specific spot positioned at the expected calculated pI of 4.77 (FIG. 1A) (20). Minor spots that were more acidic in pI were also observed. Both α-tubulin and β-tubulins undergo glutamylation and phosphorylation on their C-termini (23) that could account for such additional spots. It was previously observed monoglutamylation of Kα1 and βI-tubulin in cancer cell lines (24) and more acidic spots corresponding to these isoforms are indicated.

It was possible to exclude cross reactivity of the βV-tubulin antibody with βI-tubulin using a high resolution one-dimensional isoelectric focusing gel transferred onto nitrocellulose to analyze the expression of tubulin in microtubule pellets generated from an epothilone-B resistant cell line derived from A549 cells (25). These cells have a Gln to Glu mutation at residue 292 of βI-tubulin, which causes a loss of 0.02 unit of pI for βI-tubulin. If the βV antibody also cross-reacted with βI-tubulin, two bands with different electrophoretic mobilities would be apparent, similar to the profile shown by the Coomassie blue stain. In fact, the βV antibody reacted with a protein focusing between wild-type (pI=4.78) and mutant βI-tubulin (pI=4.76) (FIG. 1B). Thus, the βV-tubulin antibody does not cross-react with βI-tubulin. Next, to further test specificity, the βV-tubulin antibody was pre-incubated with βV- or βIII-tubulin C-terminal peptides prior to immunoblot analysis for βV-tubulin (FIG. 1C). Since the antibody-defining regions of BIII and BV are the most homologous among the tubulins, we used C-terminal peptides of BIII to confirm BV antibody specificity. As expected, pre-incubation of the βV-tubulin antibody with βV-tubulin C-terminal peptide but not with the βIII-tubulin C-terminal peptide prevented the detection of βV-tubulin. Lastly, immunoblots of Hey and A549 carcinoma cell lines were probed with βI-, βIII-, βIV-, and βV-tubulin antibodies and respective signals were normalized to those of total β-tubulin and GAPDH (FIG. 1C). The observed differences in expression levels were comparable to those revealed by mass spectrometry (20).

Figures 2A, 2B, 2C:
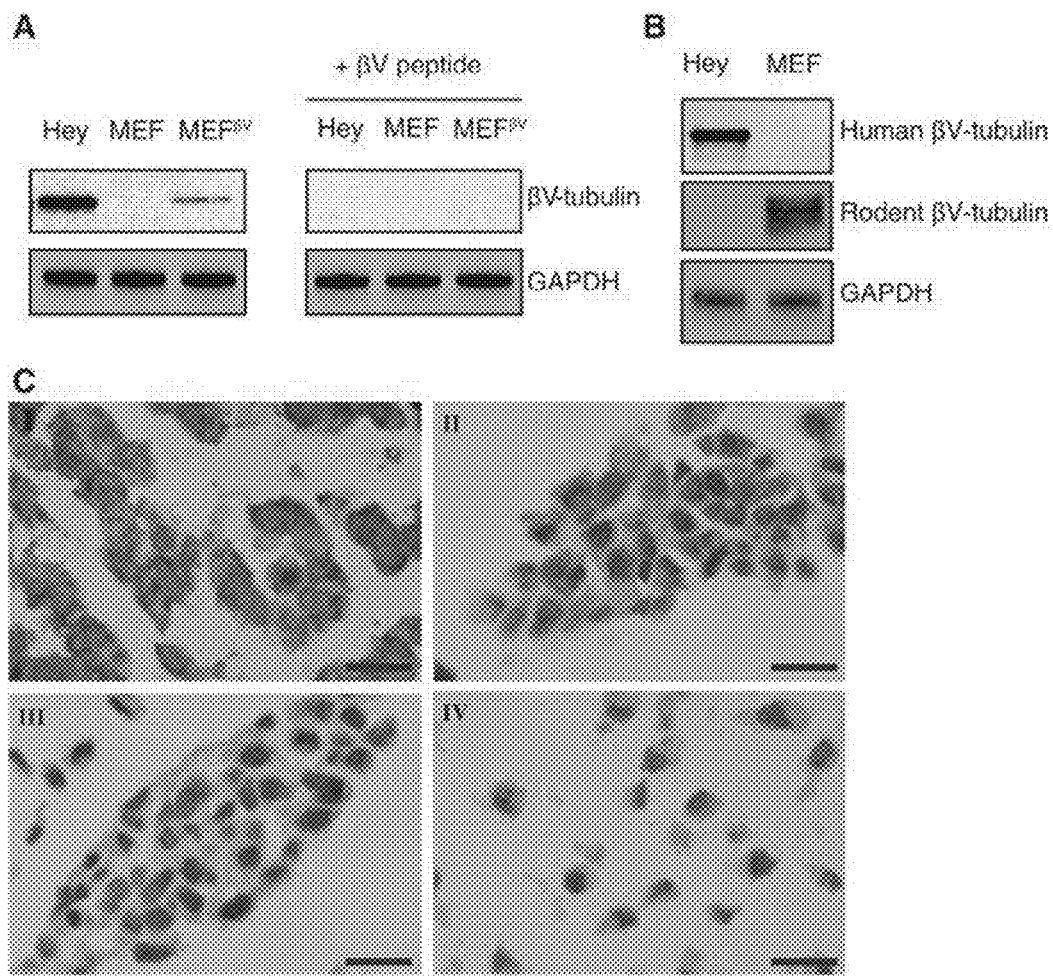
FIG. 2A-2C. Specificity of human βV-tubulin immunoreactivity in mouse embryonic fibroblasts (MEFs) expressing exogenous human βV-tubulin. A) Mouse embryonic fibroblasts transfected with empty vector or full length, human βV-tubulin (MEFβV) were immunoblotted with the βV-tubulin antibody in the absence and presence of βV-tubulin peptides. B) Immunoblot analysis of MEF and Hey cells with a rodent specific βV-tubulin monoclonal antibody. C) Immunohistochemical analysis of βV-tubulin expression in formalin-fixed paraffin-embedded cells (I) Hey cells, positive control for high expression of endogenous βV-tubulin, (II) MEFs expressing exogenous human βV-tubulin, (III) MEFs transfected with empty vector, and (IV) Hey cells incubated with secondary antibody only. All slides were counterstained with hematoxylin. Scale bars, 20 µm.

Human and mouse βV-tubulin have 97.7% overall amino acid identity, while the antigen-defining region has 79% homology. To test whether the human βV-tubulin antibody that were developed would cross react with mouse βV-tubulin, mouse embryonic fibroblasts (MEFs) were transduced with full length human βV-tubulin, or vector alone. Subsequent immunoblotting indicated that the βV-tubulin antibody was only able to detect human βV-tubulin in the transduced MEFs and not in the endogenous mouse βV-tubulin protein (FIG. 2A). The expression of endogenous mouse βV-tubulin was detected in MEF lysates using a monoclonal antibody specific to rodent βV-tubulin (FIG. 2B). This result indicated that the βV-tubulin antibody we generated is specific for the human isotype.

A BLAST protein sequence similarity search was performed with the C-terminus sequence of βV-tubulin. It was found that this sequence was similar to an internal sequence ($_{262}$EEDEEEEIDV$_{271}$) (SEQ ID NO:5) of human N-Myc oncoprotein, a protein with a MW similar to tubulin (49 kDa). In order to eliminate the possibility of cross reactivity between the two, particularly for immunohistochemical applications, immunoblot analysis was performed using the βV-tubulin antibody against recombinant full-length N-Myc protein containing a 26 kDa N-terminal GST tag, which decreases its electrophoretic mobility to an approximate MW of 80 kDa. Lysates from SH-SY5Y neuroblastoma cells that are known to overexpress N-Myc were used as a control. The βV-tubulin antibody was unable to detect N-Myc by immunoblotting, even with prolonged exposure. Immunohistochemistry performed on N-myc rich neuroblastoma tissue was negative for expression of βV-tubulin (data not shown). Therefore no cross-reactivity occurs between βV-tubulin and N-myc. This result and the non cross-reactivity of our anti-human βV-tubulin antibody with the C-terminus of mouse βV-tubulin strongly suggest that the recognized epitope involves the last two amino acid residues and the C-terminal carboxyl.

Previously published data utilizing a rodent βV-tubulin monoclonal antibody indicated that βV-tubulin is concentrated in the inner ear, localizing specifically to pillar cells and deiter cells in gerbil cochlea (5). Due to difficulties obtaining equivalent human specimens, it was not possible to confirm these results with the human antibody. To test the capability of the βV-tubulin antibody for immunohistochemistry, formalin-fixed, paraffin-embedded MEF cell pellets sections were prepared from MEFs overexpressing βV-tubulin or transduced with the empty vector. The immunohistochemical staining pattern for βV-tubulin antibody was cytoplasmic with a clean background. βV-tubulin was strongly expressed in stably-transfected MEFs and negative in vector-only transfected MEFs (FIG. 2C).

Figure 3:
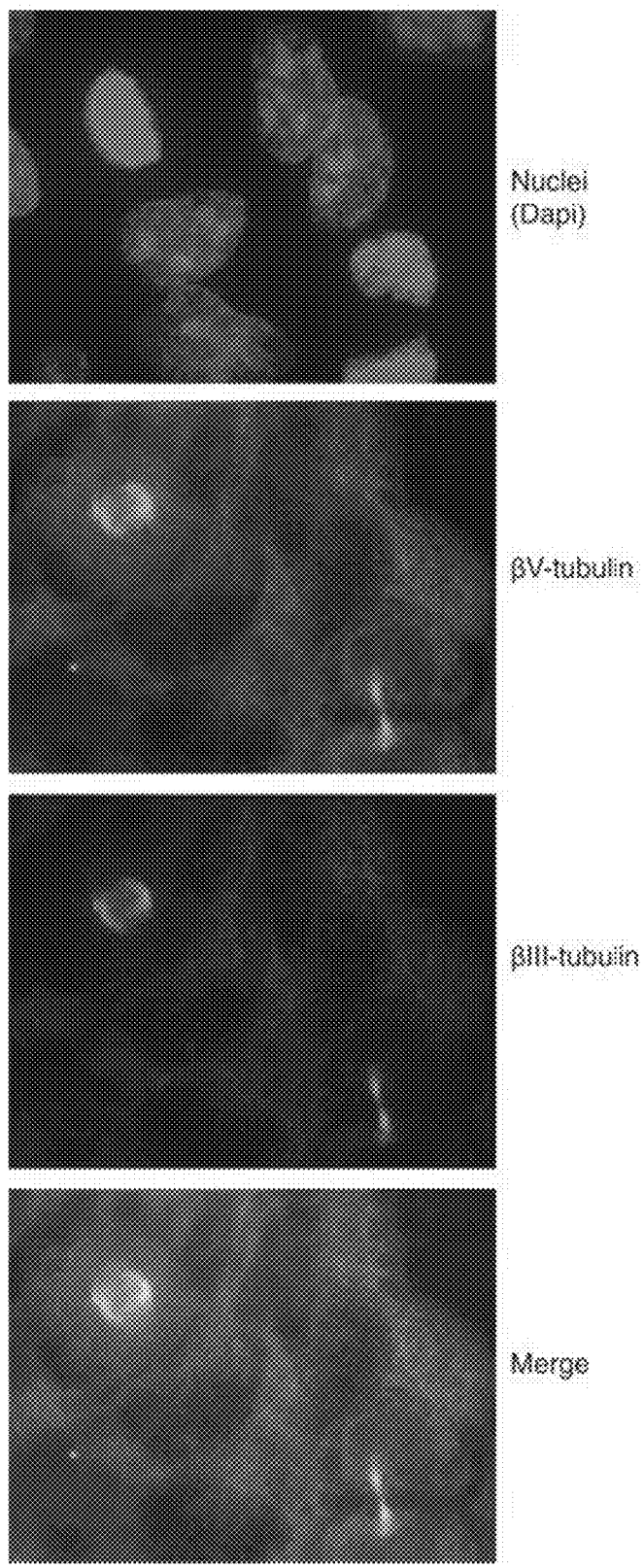
FIG. 3. Immunofluorescence of endogenous βV- and βIII-tubulin in HeLa cells. Field includes interphase and mitotic cells. From top: dapi staining of nuclei, alexa 488 labeling of βV-tubulin, alexa 555 labeling of βIII-tubulin, and merged image.

Localization of human βV-tubulin in cultured cells: The human βV-tubulin antibody generated was also evaluated by immunofluorescence in HeLa cells. Localization was contrasted with βIII-tubulin. Both βV- and βIII-tubulin had diffuse staining that localized throughout the cytoplasm of interphase cells, with intense staining of mitotic cell spindles and of the intercellular bridge in late telophase (FIG. 3). Immunofluorescence using the murine βV-tubulin antibody in NIH3T3 cells also demonstrated that βV-tubulin is concentrated at microtubule spindles and is present in the microtubule network of interphase cells (5). There may be a subtle difference in the distribution of βIII versus βV in the spindles of HeLa cells. Cytoplasmic βV-tubulin immunostaining was also observed in Hey cells, similar to the distribution observed by immunohistochemistry.

Figure 4:
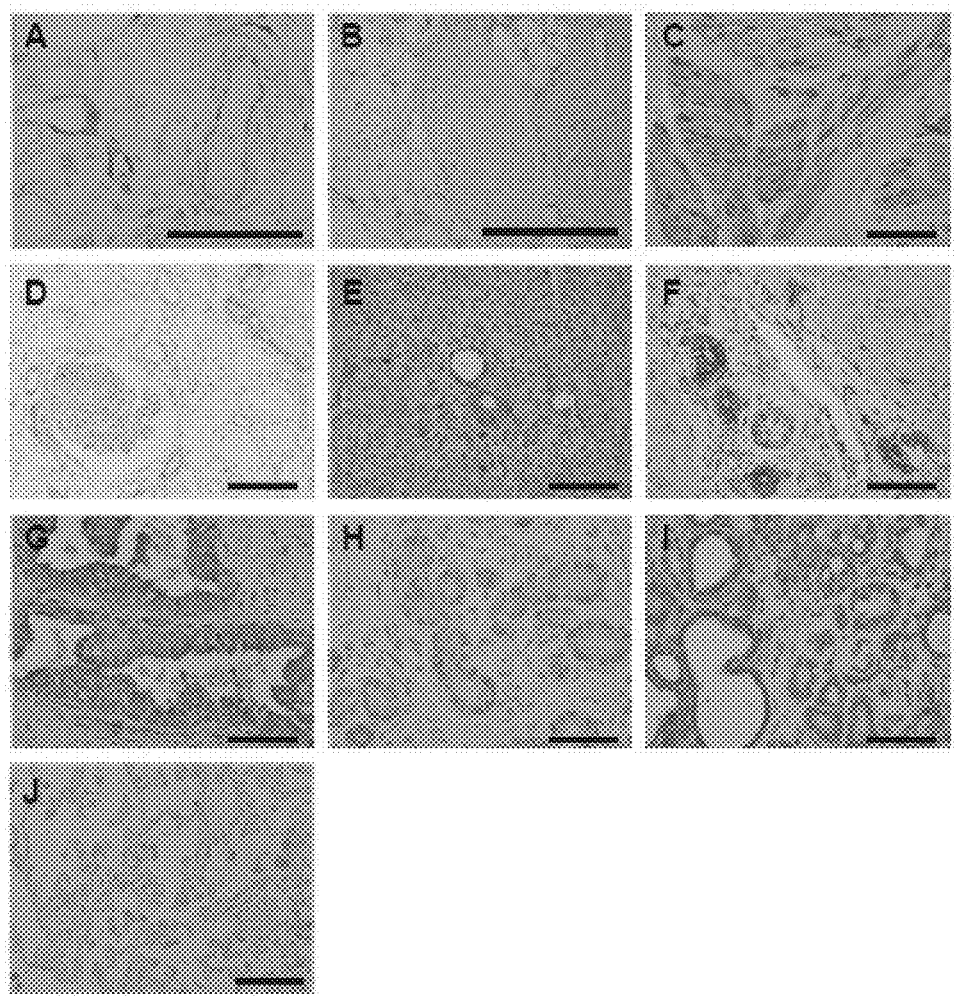
FIG. 4A-4J. Immunohistochemistry of βV-tubulin in normal human tissue. A) endothelial cells of vessels and capillaries, B) nerve fiber, C) smooth muscle, D) glomerulus and renal tubules, E) pancreatic ducts, F) bile ducts of liver; G) prostate glands, H) normal breast ducts/lobules; I) lactating breast, J) normal lung. Scale bars, 100 µm.

Immunohistochemical analysis of βV-tubulin in human tissue: The distribution of βV-tubulin protein in human tissue has never been determined due to the unavailability of a specific antibody. Using the human specific βV tubulin antibody, βV expression was determined in a variety of human normal tissue types (Table 1). As indicated by immunofluorescence, βV-tubulin showed a cytoplasmic pattern of staining by immunohistochemistry, as shown in FIG. 4.

TABLE 1

Distribution of βV-tubulin in Normal Tissues by Immunohistochemistry

| Tissue | | Intensity |
|---|---|---|
| Skin | Sebaceous glands | +++ |
| | Squamous epithelium | + (variable) |
| | Basal cells | + |
| Muscle | Smooth muscle | +++ |
| | Skeletal muscle | ++ |
| | Cardiac Muscle | ++ |
| Blood vessel | Endothelial cells | +++ |
| | Smooth muscle | ++ |
| GI Tract ¶ | Epithelium | − |
| Liver | Hepatocytes | − |
| | Bile ducts | ++ |
| Pancreas | Ducts | + |
| | Islets | ++ |
| | Acini | − |
| Kidney | Renal tubules | − to ++ (variable) |
| | Glomeruli | ++ |
| Testis | Seminiferous tubules | − |
| | Mature germ cells | − |
| | Immature germ cells | ++ |
| | Sertoli cells | − |
| Prostate | Glandular cells | ++ (variable) |
| | Basal cells | − |
| Mammary glands | Luminal cells | − |
| | Lactating secretory cells | ++ |
| | Myoepithelial cells | +++ |
| Ovary | Surface epithelium | − |
| | Stromal cells | + |
| Fallopian tube | Epithelium | − |
| Lung | Pneumocytes | − |
| | Respiratory epithelium | |
| Thyroid | Follicular cells | − to ++ (variable) |
| Adrenal gland | Cortex and medulla | − |
| Salivary gland | Acini | + (variable) |
| | Ducts | ++ |
| Nerve | Neuronal cells | − |

In general, βV-tubulin was consistently expressed in the endothelial cells of the blood vessels (FIG. 4A), myocytes and cells with muscle differentiation. βV-tubulin was expressed in muscles of all three types with particularly strong expression in smooth muscle. Specialized cells such as myoepithelial cells of the breast and myoid cells of the testis showed strong βV-tubulin staining, consistent with their muscle differentiation. The glomeruli of the kidney have specialized tuft-like vascular structure composed of fenestrated endothelium, podocytes and mesangial cells. βV-tubulin showed an interesting mosaic pattern outlining the glomeruli. This pattern was correlated with the positive expression in endothelial cells and mesangial cells, a specialized cell type with muscle differentiation. βIII-tubulin is known to be highly expressed in neuronal cells, and is currently used as a marker of neuronal differentiation (26). βV-tubulin, unlike βIII-tubulin, was not expressed in nerves (FIG. 4B). To confirm the findings by immunohistochemistry, immunoblot analysis of a human microvascular endothelial cell line (HMEC-1) was used. βV-tubulin, but not βIII was expressed minimally in these cells.

Moderate staining was consistently observed in cells with secretory/transport function such as renal tubules, bile ducts of the liver, pancreatic exocrine ducts and ducts of salivary glands (Table 1 and FIG. 4). These cells transportions and water and have small molecule exchange/secretion/absorption functions during transport processes, suggesting the possibility that βV-tubulin participates in transport function, and certain ion or small molecule exchange. βV-tubulin was also strongly expressed in sebaceous glands of the skin and variably expressed in prostate glandular epithelium and thyroid follicular cells, which are epithelial tissues with secretary functions. In contrast, βV staining was not detected in the epithelium of the GI tract (stomach, duodenum, gall bladder, small and large intestine), hepatocytes, ovarian surface epithelium and pneumocytes. In normal breast tissue, βV-tubulin was absent in luminal epithelial cells of the ducts/lobules, however, it was strongly expressed in the luminal cells of the breast during lactation (FIG. 4H-I) This specific expression of βV may be is acquired to meet the demanding secretory needs of the breast during lactation. In addition, macrophages in various tissues showed positive staining for βV-tubulin. Macrophages are inflammatory mediators with secretory function, therefore βV-tubulin expression in macrophages is consistent with the likely secretory-related functions of this tubulin isotype.

Figure 5:
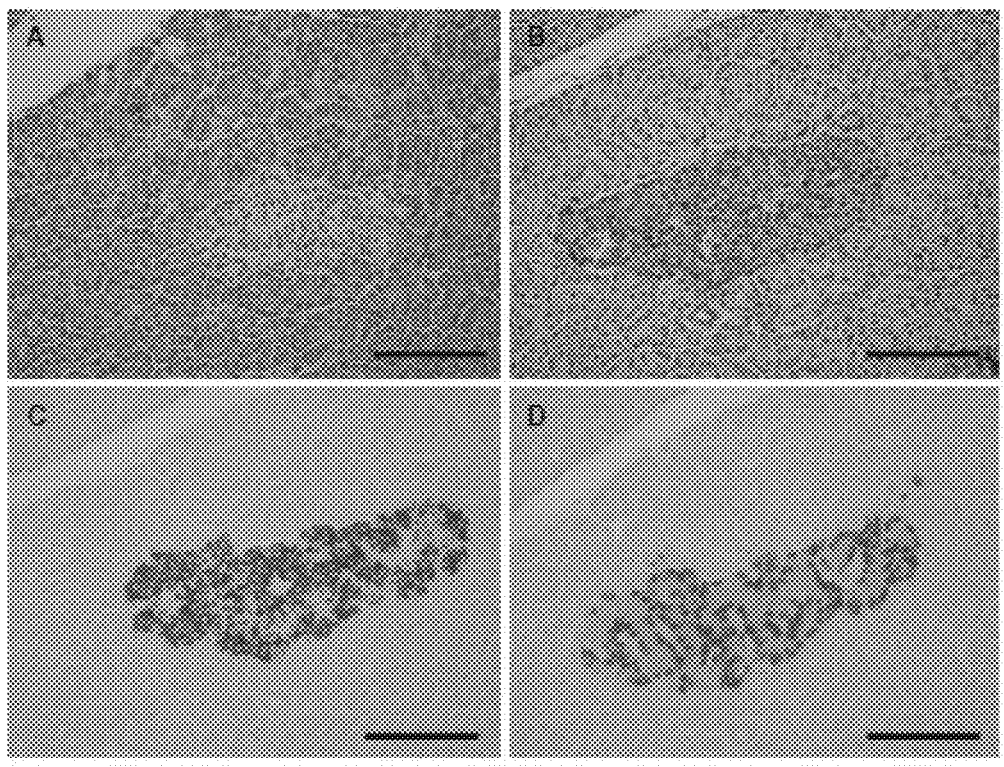
FIG. 5A-5D. Immunohistochemistry of βV-tubulin in pancreatic islets. A) Hematoxylin and eosin, B) βV-tubulin, C) insulin, D) glucagon. Scale bars, 100 µm.
Figure 6:
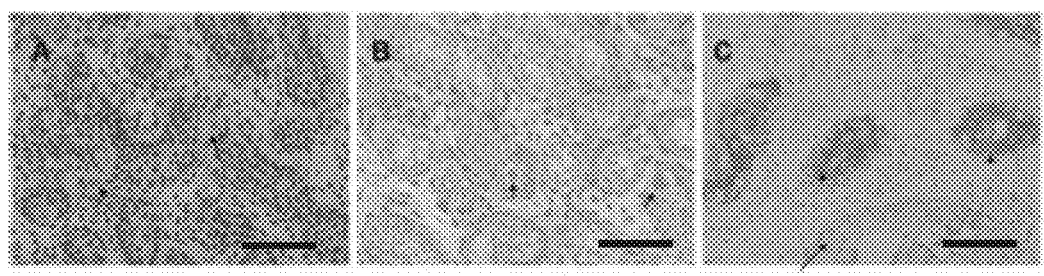
FIG. 6A-6C. Immunohistochemistry βV-tubulin in the germ cells of immature testis. A) Hematoxylin and eosin staining of a tissue section from a one year old child with testis cryptorchidism. B) βV-tubulin was expressed in the germ cells—spermatogonia in the seminiferous tubules (arrows). Sertoli cells were negative. The surrounding outer myoid cells were positive staining for βV-tubulin due to their muscle differentiation. C) An adult testis with intratubular germ cells neoplasia (ITGCN). βV-tubulin was strongly expressed in ITGCN (arrowheads). Normal seminiferous tubules in the background were negative for βV-tubulin (arrow). Scale bars, 100 µm.

Expression of βV-tubulin in pancreatic islets and testis: Interestingly, while βV was largely negative in pancreatic parenchyma (exocrine glands), it was positively expressed in pancreatic islets (FIG. 4E and FIG. 5). Pancreastic islets are endocrine components of the pancreas that are composed of alpha and beta cells that are responsible for the secretion of glucagon and insulin, respectively. It was possible to compare the immunostaining pattern of βV-tubulin with that of glucagon and insulin using specific antibodies on serially sectioned pancreatic tissue (FIG. 5). BV-positive cells were localized around the periphery of the islets in a region that qualitatively correlates with the localization of glucagon-stained alpha cells (FIG. 5D). Thus, these data suggest that the glucagon-producing alpha cells may require βV-tubulin for a specific function.

βV-tubulin also exhibited an interesting pattern in testis. A testicular biopsy from a child with cryptochidism showed βV-tubulin positivity highlighting spermatogonia in the seminiferous tubules (FIG. 6). In tissue samples of intratubular germ cell neoplasia (ITGCN), surprisingly specific strong expression of βV-tubulin was observed in the neoplastic germ cells, while in contrast, normal seminiferous tubules were negative. Although the number of cases tested was limited (3/3), they support that βV-tubulin may be used to identify ITGCN. To date, there is no diagnostic immunohistochemical marker of this entity.

Figure 7:
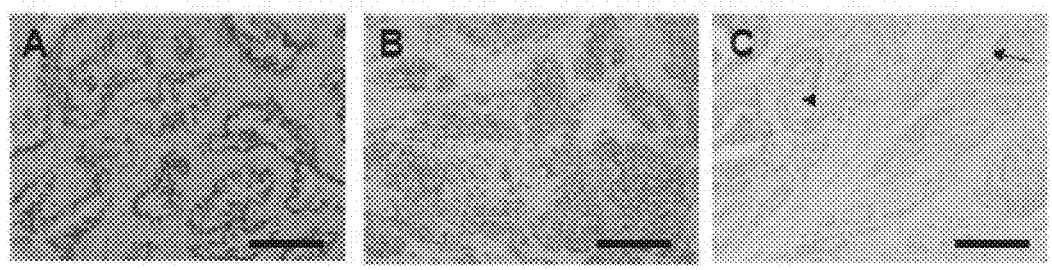
FIG. 7A-7C. Immunohistochemistry of βV-tubulin in human malignancy. βV-tubulin was strongly expressed in A) lung adenocarcinoma and B) invasive breast cancer. C) loss of βV-tubulin in infiltrating prostate adenocarcinoma and perineural invasion of the adenocarcinoma. A nerve fiber that is negative for βV-tubulin is indicated by the arrowhead. Variable expression of βV-tubulin in normal prostate glands is present in the upper left. Endothelial cells lining blood vessels positive for βV-tubulin are indicated (arrow), Scale bars, 100 µm.

Expression of βV-tubulin in human cancer: Since tumorigenesis often causes altered differentiation of affected cells, as is the case with the neuronal-specific βIII-tubulin isotype that is expressed in numerous malignancies, the expression of βV-tubulin was evaluated in a small cohort of carcinomas including breast, lung, prostate and ovary. It was found that, in contrast to the negative staining in their normal counterparts, lung, breast and ovarian cancers (the latter not shown), had aberrant βV-tubulin expression. Conversely, while normal prostate glands showed variable βV-tubulin staining, expression was completely lost in prostate cancer (FIG. 7).

Immunobloting for βV-tubulin was also performed in a series of lung (NSCLC), ovarian, and breast cancer cell lines to determine if there was a histological association with its expression. βV-tubulin was expressed in all but one cell line, although at highly variable levels, supporting previous studies suggesting that it is ubiquitously expressed in cancer cell lines (27). Thus these data are consistent with the immunohistochemical data obtained for lung, ovarian and breast cancer.

A study was conducted of βV-tubulin expression in 32 cases of breast cancers with various differentiation states. βV-tubulin was aberrantly expressed in ten cases (30%), of which nine were poorly differentiated, suggesting that expression is associated with maligant transformation and high tumor grade. Thus, the data indicate that βV-tubulin is abberrantly expressed in lung, ovarian and breast cancer and collectively imply that like βIII-tubulin, βV-tubulin has irregular expression in transformed cells.

Discussion

Several studies have established that mammalian microtubules will incorporate all available tubulin isotypes as evidenced by immunofluorescence using isotype specific antibodies and secondly, by transfection of non-mammalian isotypes into mammalian cells (28-30). βV-tubulin is a minor tubulin isotype, composing less than 10% of the total tubulin in most tissues in the chicken, (31), less than 20% in mouse embryonic fibroblasts, and less than approximately 7% of total tubulin in Chinese hamster ovary cells (28, 30, 31).

Numerous studies have documented overexpression of βIII-tubulin in different malignancies, and its utility as a marker of poor survival and, in some cases response to therapy (7,9). This has prompted widespread interest in characterizing the expression of other tubulin isoforms in human malignancies. In the absence of a commercially available specific βV-tubulin antibody, many of the studies to date have employed overexpression or RNA-based knockdown techniques to modulate βV in numerous cell lines, without a real appreciation of the tissue-specific expression of this isotype in normal tissue. A previous qRT-PCR study reported ubiquitous expression of βV-tubulin in human tissue (15), however this was not found by immunohistochemistry. It is possible that the levels of βV-tubulin protein in the RT-PCR positive tissues are extremely low, or that the ubiquitous expression was an artefact due to contamination with a βV-tubulin positive cell type, such as endothelial cells or macrophages, since laser-capture microdissection was not performed.

To circumvent this inherent problem with mRNA expression profiling, it was sought to generate a human-specific βV-tubulin antibody that could be used to delineate the repetoir of expression in normal and malignant tissue, and as such provide evidence about the potential function of this specific tubulin isoform.

Unlike βIII tubulin that is normally expressed only in neuronal tissue and cells, βV was expressed in a wide range of human non-neuronal cell and tissue types. The observation that βV-tubulin was preferentially expressed in cells with a secretory function, such as pancreatic ductal cells, was unexpected. One of the functions of microtubules is to move secreted proteins within cells. Colchicine, a microtubule destabilizing agent that interacts with the tubulin dimer, has been shown to inhibit the secretion of several proteins from secretory tissues. Specifically, colchicine inhibits the secretion of thyroid hormones from thyroid epithelial cells, lipoproteins from liver cells, insulin from pancreatic islet cells, $HCO_3$ from pancreatic ducts, and apolipoprotein E from macrophages (32-35). Interestingly, cell types that constitute the pancreastic islet, salivary ducts and bile duct showed positive staining for βV-tubulin, reinforcing the view that there are isotype-specific functions for tubulins.

The data from tumor tissue indicates interesting alterations in the expression of βV in normal, versus malignant breast, lung, ovary, and prostate tissue. Specifically, βV was undetectable in epithelial cells, yet was aberrantly expressed in approximately one-third of invasive breast carcinomas analyzed. Similarly, βV-tubulin was not expressed in normal lung pneumocytes or ovarian epithelium, however, some lung and ovarian cancers were positive. Conversely, while variably expressed in normal prostate glands, βV-tubulin expression was lost in prostate cancer.

Therefore, similar to the expression of βIII that occurs in malignant cells versus normal cells, there also appears to be a trend toward reversal of βV-tubulin expression during malignancy. Thus, it is plausible that the altered expression in malignant cells reflects an inherent change in the differentiation status of the normal tissue, such that βV-tubulin transcripts that are normally not expressed in a given cell type become expressed; while in tissues that normally expresses βV-tubulin, transcripts are silenced.

Overexpression of mouse βV-tubulin, like βIII, has been demonstrated to confer resistance to Taxol in cells, (11, 16, 19) although βV-tubulin was thought to confer more deleterious effects on cell division (36). In contrast, the overexpression of βI- βII-, βIV, or βVI-tubulin had no effect on microtubule assembly or drug resistance when overexpressed in cells (16, 19). βV-tubulin, like βIII, is implicated in poor prognosis for some malignancies and poor response to therapy. Moreover, the unique profile of βV-tubulin expression characterized in several malignancies here lends support to the notion that altered expression of this tubulin isoform may be associated with tumorigenesis.

REFERENCES

1. Joshi H C, Yen T J, Cleveland D W: In vivo coassembly of a divergent beta-tubulin subunit (c beta 6) into microtubules of different function, J Cell Biol 1987, 105:2179-2190
2. Luduena R F: Multiple forms of tubulin: different gene products and covalent modifications, Int Rev Cytol 1998, 178:207-275
3. Miller L M, Xiao H, Burd B, Horwitz S B, Angeletti R H, Verdier-Pinard P: Methods in tubulin proteomics, Methods Cell Biol 2010, 95:105-126
4. Verdier-Pinard P, Pasquier E, Xiao H, Burd B, Villard C, Lafitte D, Miller L M, Angeletti R H, Horwitz S B, Braguer D: Tubulin proteomics: towards breaking the code, Anal Biochem 2009, 384:197-206
5. Banerjee A, Jensen-Smith H, Lazzell A, Prasad V, Elguezabal G, Hallworth R, Luduena R F: Localization of betav tubulin in the cochlea and cultured cells with a novel monoclonal antibody, Cell Motil Cytoskeleton 2008, 65:505-514
6. Orr G A, Verdier-Pinard P, McDaid H, Horwitz S B: Mechanisms of Taxol resistance related to microtubules, Oncogene 2003, 22:7280-7295
7. Kavallaris M: Microtubules and resistance to tubulin-binding agents, Nat Rev Cancer 2010, 10:194-204
8. Seve P, Dumontet C: Class III beta tubulin expression in nonsmall cell lung cancer, Rev Mal Respir 2010, 27:383-386
9. Ferrandina G, Zannoni G F, Martinelli E, Paglia A, Gallotta V, Mozzetti S, Scambia G, Ferlini C: Class III beta-tubulin overexpression is a marker of poor clinical outcome in advanced ovarian cancer patients, Clin Cancer Res 2006, 12:2774-2779
10. Seve P, Dumontet C: Is class III beta-tubulin a predictive factor in patients receiving tubulin-binding agents?, Lancet Oncol 2008, 9:168-175
11. Kavallaris M, Kuo D Y, Burkhart C A, Regl D L, Norris M D, Haber M, Horwitz S B: Taxol-resistant epithelial ovarian tumors are associated with altered expression of specific beta-tubulin isotypes, J Clin Invest 1997, 100:1282-1293
12. Seve P, Reiman T, Lai R, Hanson J, Santos C, Johnson L, Dabbagh L, Sawyer M, Dumontet C, Mackey J R: Class III beta-tubulin is a marker of paclitaxel resistance in carcinomas of unknown primary site, Cancer Chemother Pharmacol 2007, 60:27-34
13. McCarroll J A, Gan P P, Liu M, Kavallaris M: betaIII-tubulin is a multifunctional protein involved in drug sensitivity and tumorigenesis in non-small cell lung cancer, Cancer Res 2010, 70:4995-5003
14. Lee K M, Cao D, Itami A, Pour P M, Hruban R H, Maitra A, Ouellette M M: Class III beta-tubulin, a marker of resistance to paclitaxel, is overexpressed in pancreatic ductal adenocarcinoma and intraepithelial neoplasia, Histopathology 2007, 51:539-546
15. Leandro-Garcia L J, Leskela S, Landa I, Montero-Conde C, Lopez-Jimenez E, Leton R, Cascon A, Robledo M, Rodriguez-Antona C: Tumoral and tissue-specific expression of the major human beta-tubulin isotypes, Cytoskeleton (Hoboken) 2010, 67:214-223
16. Bhattacharya R, Cabral F: Molecular basis for class V beta-tubulin effects on microtubule assembly and paclitaxel resistance, J Biol Chem 2009, 284:13023-13032
17. Ganguly A, Yang H, Cabral F: Paclitaxel-dependent cell lines reveal a novel drug activity, Mol Cancer Ther 2010, 9:2914-2923
18. Martello L A, Verdier-Pinard P, Shen H J, He L, Torres K, Orr G A, Horwitz S B: Elevated levels of microtubule destabilizing factors in a Taxol-resistant/dependent A549 cell line with an alpha-tubulin mutation, Cancer Res 2003, 63:1207-1213
19. Bhattacharya R, Cabral F: A ubiquitous beta-tubulin disrupts microtubule assembly and inhibits cell proliferation, Mol Biol Cell 2004, 15:3123-3131
20. Verdier-Pinard P, Shahabi S, Wang F, Burd B, Xiao H, Goldberg G L, Orr G A, Horwitz S B: Detection of human betaV-tubulin expression in epithelial cancer cell lines by tubulin proteomics, Biochemistry 2005, 44:15858-15870
21. Verdier-Pinard P, Wang F, Martello L, Burd B, Orr G A, Horwitz S B: Analysis of tubulin isotypes and mutations from taxol-resistant cells by combined isoelectrofocusing and mass spectrometry, Biochemistry 2003, 42:5349-5357
22. Miller L M, Menthena A, Chatterjee C, Verdier-Pinard P, Novikoff P M, Horwitz S B, Angeletti R H: Increased levels of a unique post-translationally modified betaIVb-tubulin isotype in liver cancer, Biochemistry 2008, 47:7572-7582
23. Verhey K J, Gaertig J: The tubulin code, Cell Cycle 2007, 6:2152-2160
24. Verdier-Pinard P, Wang F, Burd B, Angeletti R H, Horwitz S B, Orr G A: Direct analysis of tubulin expression in cancer cell lines by electrospray ionization mass spectrometry, Biochemistry 2003, 42:12019-12027
25. Yang C P, Verdier-Pinard P, Wang F, Lippaine-Horvath E, He L, Li D, Hofle G, Ojima I, Orr G A, Horwitz S B: A highly epothilone B-resistant A549 cell line with mutations in tubulin that confer drug dependence, Mol Cancer Ther 2005, 4:987-995
26. Lee M K, Tuttle J B, Rebhun L I, Cleveland D W, Frankfurter A: The expression and posttranslational modification of a neuron-specific beta-tubulin isotype during chick embryogenesis, Cell Motil Cytoskeleton 1990, 17:118-132

27. Bhattacharya R, Frankfurter A, Cabral F: A minor beta-tubulin essential for mammalian cell proliferation, Cell Motil Cytoskeleton 2008, 65:708-720
28. Lopata M A, Cleveland D W: In vivo microtubules are copolymers of available beta-tubulin isotypes: localization of each of six vertebrate beta-tubulin isotypes using polyclonal antibodies elicited by synthetic peptide antigens, J Cell Biol 1987, 105:1707-1720
29. Lewis S A, Gu W, Cowan N J: Free intermingling of mammalian beta-tubulin isotypes among functionally distinct microtubules, Cell 1987, 49:539-548
30. Sawada T, Cabral F: Expression and function of beta-tubulin isotypes in Chinese hamster ovary cells, J Biol Chem 1989, 264:3013-3020
31. Sullivan K F, Havercroft J C, Machlin P S, Cleveland D W: Sequence and expression of the chicken beta 5- and beta 4-tubulin genes define a pair of divergent beta-tubulins with complementary patterns of expression, Mol Cell Biol 1986, 6:4409-4418
32. Kockx M, Guo D L, Huby T, Lesnik P, Kay J, Sabaretnam T, Jary E, Hill M, Gaus K, Chapman J, Stow J L, Jessup W, Kritharides L: Secretion of apolipoprotein E from macrophages occurs via a protein kinase A and calcium-dependent pathway along the microtubule network, Circ Res 2007, 101:607-616
33. Williams J A, Wolff J: Colchicine-binding protein and the secretion of thyroid hormone, J Cell Biol 1972, 54:157-165
34. Montague W, Howell S L, Green I C: Insulin release and the microtubular system of the islets of Langerhans. Identification and characterization of tubulin-like protein, Biochem J 1975, 148:237-243
35. Stein O, Sanger L, Stein Y: Colchicine-induced inhibition of lipoprotein and protein secretion into the serum and lack of interference with secretion of biliary phospholipids and cholesterol by rat liver in vivo, J Cell Biol 1974, 62:90-103
36. Bhattacharya R, Yang H, Cabral F: Class V beta-tubulin alters dynamic instability and stimulates microtubule detachment from centrosomes, Mol Biol Cell 2011, 22:1025-1034

What is claimed is:

1. A method for determining whether a prostate sample from a subject is cancerous, comprising
    contacting the sample with an antibody against human βV-tubulin, or a fragment thereof capable of binding to human βV-tubulin, wherein the antibody or fragment is directed against an epitope comprising GEE-AFEDEEEEIDG (SEQ ID NO:1) or CGEE-AFEDEEEEIDG (SEQ ID NO:2),
    quantitating an amount of antibody or fragment bound,
    comparing the amount of bound antibody or fragment to a predetermined control amount in healthy prostate tissue, and
    determining whether the prostate sample is cancerous, wherein the amount of antibody or fragment bound equal to or in excess of the predetermined control amount indicates that the prostate sample is not cancerous, and the amount of antibody or fragment bound below the predetermined control amount indicates that the prostate sample is cancerous.

2. The method of claim 1, wherein the antibody or fragment does not bind human βIII-tubulin.

3. The method of claim 1, wherein the antibody or fragment does not bind a protein comprising YEDDEEESEAQGPK (SEQ ID NO:4) or a protein comprising CYED-DEEESEAQGPK (SEQ ID NO:3).

4. The method of claim 1, wherein the antibody or fragment does not bind human βI-tubulin.

5. The method of claim 1, wherein the antibody or fragment does not bind human N-Myc oncoprotein.

6. The method of claim 1, wherein the antibody is a monoclonal antibody.

7. The method of claim 1, wherein the antibody is a human antibody, a humanized antibody or a chimeric antibody.

8. The method of claim 1, wherein the fragment comprises a Fab, a Fab', a F(ab')2, a Fd, a Fv, a complementarity determining region (CDR), or a single-chain antibody (scFv).

9. The method of claim 1, further comprising treating the subject determined to have a cancerous prostate with an anticancer medication.

* * * * *